(12) United States Patent
Hongou et al.

(10) Patent No.: US 10,123,765 B2
(45) Date of Patent: Nov. 13, 2018

(54) ULTRASOUND PROBE AND ULTRASOUND DIAGNOSTIC APPARATUS

(75) Inventors: Hironobu Hongou, Otawara (JP); Toru Hirano, Otawara (JP); Isao Uchiumi, Nasushiobara (JP); Masaaki Ishitsuka, Nasushiobara (JP); Takayuki Shiina, Otawara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 1218 days.

(21) Appl. No.: 12/977,905

(22) Filed: Dec. 23, 2010

(65) Prior Publication Data

US 2011/0172537 A1    Jul. 14, 2011

(30) Foreign Application Priority Data

Jan. 12, 2010  (JP) .................. 2010-003713

(51) Int. Cl.
  *A61B 8/00*     (2006.01)
  *G01S 15/89*    (2006.01)
  *G10K 11/34*    (2006.01)
  *G01S 7/52*     (2006.01)

(52) U.S. Cl.
  CPC ............. *A61B 8/00* (2013.01); *A61B 8/54* (2013.01); *G01S 7/5208* (2013.01); *G01S 15/8915* (2013.01); *G01S 15/8927* (2013.01); *G01S 15/8979* (2013.01); *G10K 11/345* (2013.01); *G01S 7/52066* (2013.01)

(58) Field of Classification Search
  USPC ..................................................... 600/447
  See application file for complete search history.

(56) References Cited

U.S. PATENT DOCUMENTS 5,617,862 A  *  4/1997  Cole et al. .................... 600/459
6,013,032 A      1/2000  Savord
6,142,946 A  *  11/2000  Hwang .................... A61B 8/00
                                                              600/459

(Continued)

FOREIGN PATENT DOCUMENTS

JP    2005-034633 A    2/2005
JP    2005-270423 A    10/2005

(Continued)

*Primary Examiner* — Michael Carey
*Assistant Examiner* — Shahdeep Mohammed
(74) *Attorney, Agent, or Firm* — Kenichiro Yoshida

(57) ABSTRACT

The present embodiment relates to an ultrasound probe having a first ultrasound vibrator group and a second ultrasound vibrator group, comprising a plurality of matrix switches and an adder. The ultrasound probe has a mode to send ultrasound to a predetermined observation point within a subject by the first ultrasound vibrator group, and to receive ultrasound echoes reflected within the subject by the second ultrasound vibrator group. The plurality of matrix switches extract, based on the distance between the second ultrasound vibrator group and the observation point, a plurality of ultrasound echoes having substantially the same phase from a plurality of ultrasound echoes output by the second ultrasound vibrator group. The adder adds the plurality of ultrasound echoes extracted by the plurality of matrix switches for each of the matrix switches and outputs them.

5 Claims, 14 Drawing Sheets

(56) References Cited

U.S. PATENT DOCUMENTS

| | | | |
|---|---|---|---|
| 2003/0036702 A1* | 2/2003 | Davidsen | A61B 8/00 600/437 |
| 2006/0058656 A1 | 3/2006 | Kristofferson et al. | |
| 2006/0079779 A1* | 4/2006 | Takimoto | 600/447 |
| 2007/0016048 A1* | 1/2007 | Baba et al. | 600/447 |
| 2009/0005684 A1* | 1/2009 | Kristoffersen et al. | 600/447 |

FOREIGN PATENT DOCUMENTS

| | | |
|---|---|---|
| JP | 2007-167445 A | 7/2007 |
| JP | 2008-018087 A | 1/2008 |

\* cited by examiner

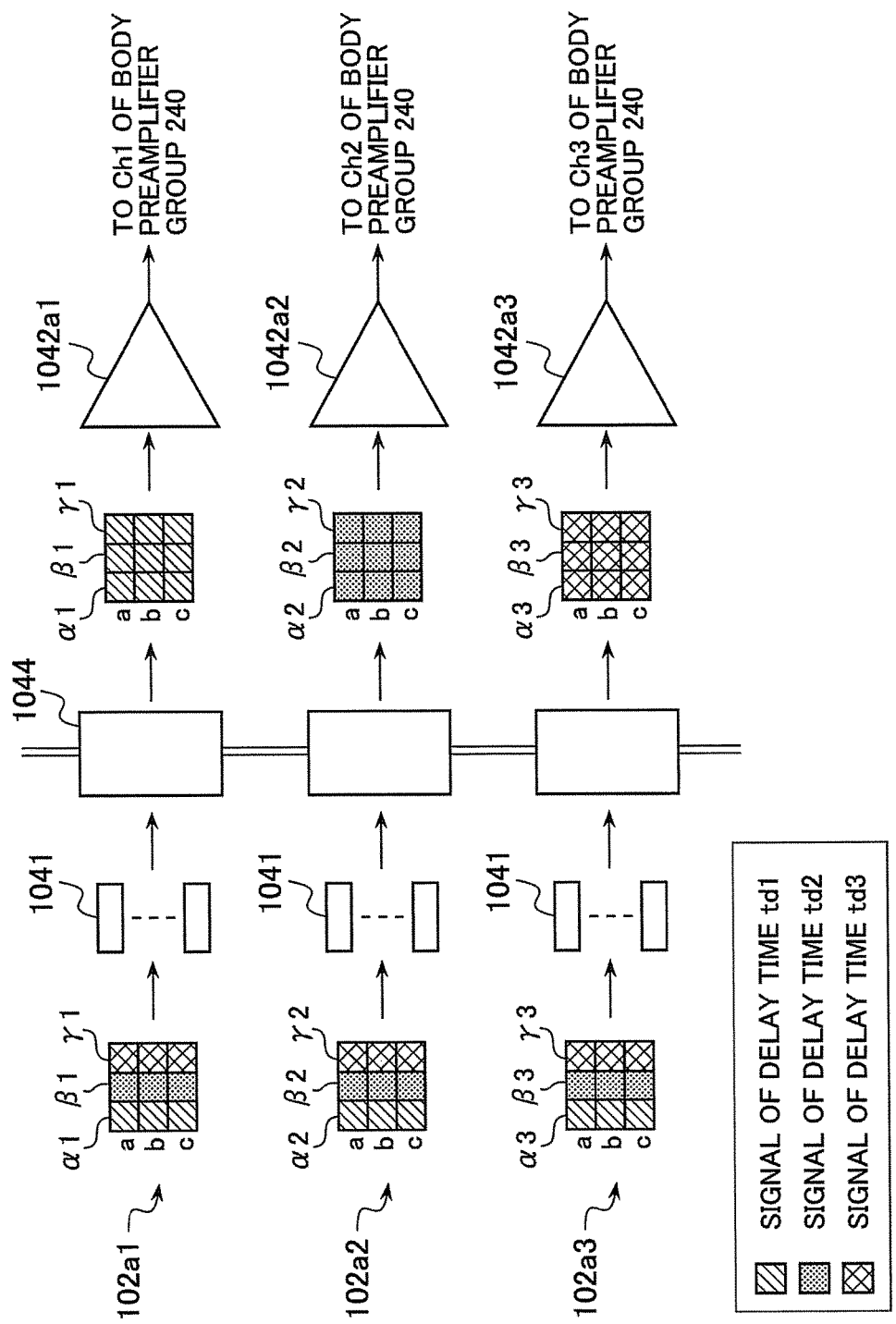

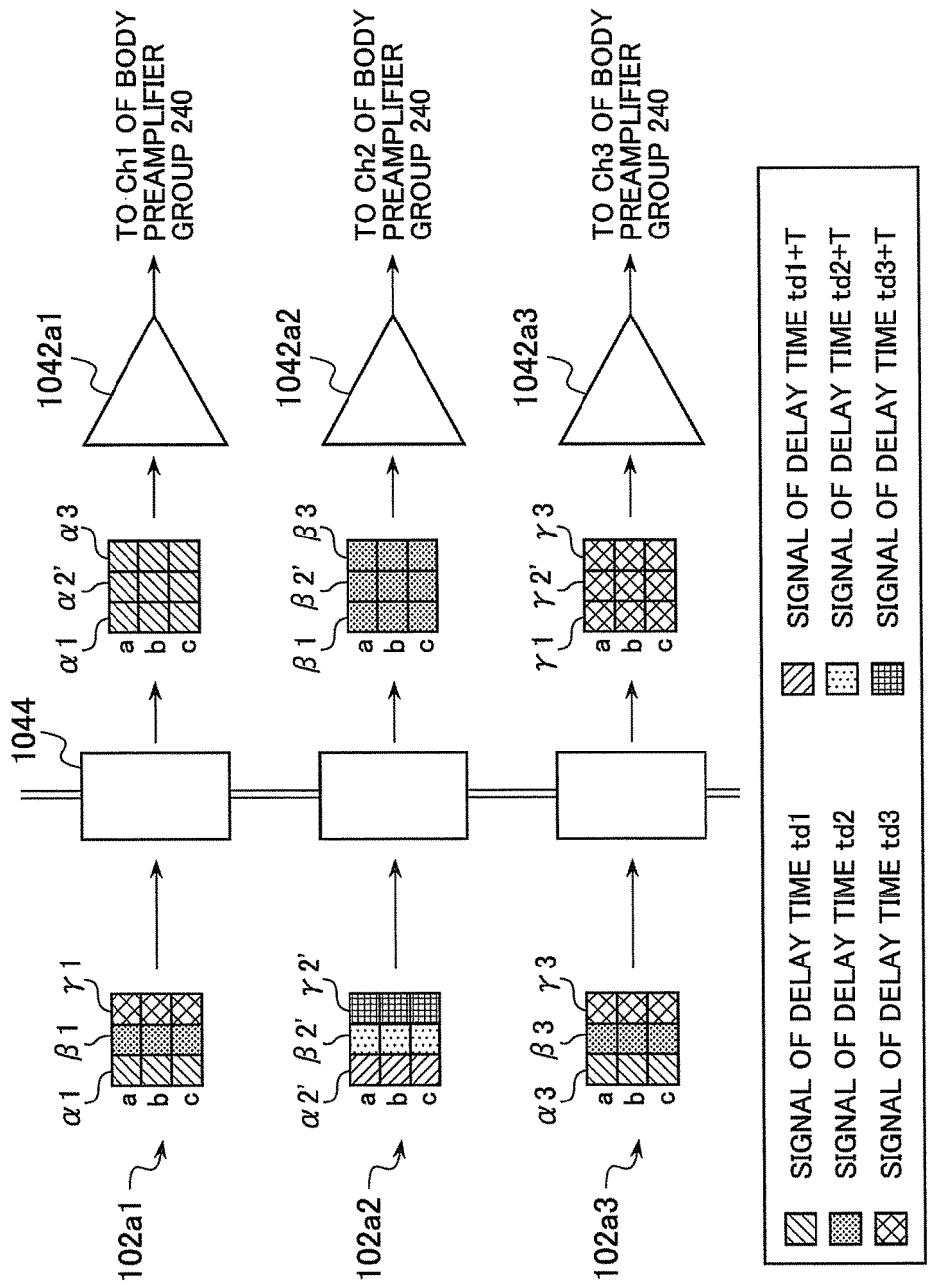

ULTRASOUND PROBE AND ULTRASOUND DIAGNOSTIC APPARATUS

CROSS-REFERENCE TO RELATED APPLICATION

This application is based upon and claims the benefit of priority from Japanese Patent Application No. 2010-003713, filed Jan. 12, 2010; the entire contents of which are incorporated herein by reference.

FIELD

The present embodiment relates to an ultrasound probe that is connected to an ultrasound diagnostic apparatus and that sends and receives ultrasound to/from a subject, and particularly to a technique to reduce the number of signal lines within a probe cable while maintaining a wide dynamic range without being limited by any restriction on the performance of electronic circuits.

BACKGROUND

In recent years, in ultrasound 2-dimensional (2D) array probes, etc., electronic circuits have been embedded in a probe head in order to perform generation of the shape of transmitter pulses, and amplification of received echoes (received signals)/partial beamforming. An ultrasound diagnostic apparatus using such an ultrasound 2D array probe is described, for example, in Japanese Unexamined Patent Application Publication No. 2007-167445.

In an ultrasound diagnostic apparatus body to which such an ultrasound probe is connected via a probe connector, ultrasound echo signals subjected to reception delay and adding processing, are amplified by a unit preamplifier group. The amplified ultrasound echo signals are matched for timing in a reception delay adding circuit, detected in a signal-processing part in order to extract an envelope, and a coordinate transform is performed in an image-processing part, subjected to appropriate processing for the image display, and displayed on a display part. With this, form information regarding the inside of the object to be observed is displayed in real time.

Configurations of a conventional ultrasound 2D array probe and ultrasound diagnostic apparatus are described with reference to FIG. 9 and FIG. 10. FIG. 9 is a functional block diagram illustrating the configuration of a general ultrasound diagnostic apparatus. FIG. 10 is a block diagram of a channel control circuit in the conventional ultrasound 2D array probe.

An ultrasound vibrator group 102 is comprised, for example, by being aligned in arrays of N M, and sends and receives ultrasound to/from an object to be observed O (for example, heart). A pulsar group 101 is connected to the ultrasound vibrator group 102, and drives the ultrasound vibrator group 102 in accordance with different timings generated in a control circuit within a probe handle 100 in order to generate ultrasound beams having predetermined directionality. With this, the ultrasound beams are irradiated towards the object to be observed O from the ultrasound vibrator group 102 in accordance with electrical signals from the pulsar group 101.

The ultrasound beams sent from the ultrasound vibrator group 102 reflect, in response to structures and movements within the object to be observed O, at interfaces with different acoustic impedance such as boundaries, etc., of structural objects within the object to be observed O. A preamplifier group 103 performs low noise amplification or buffering, etc. in order to adequately transmit the imperceptible ultrasound echo signals that are received by the ultrasound vibrator group 102. A channel control circuit 104 provides, by a sub-array reception beamformer group 1041 that is embedded (see FIG. 10), the output signals from the aforementioned plurality of preamplifier groups 103 as one group with a delay time, adds these signals by an adder 1042 that is embedded (see FIG. 10), and outputs the resultant signals to the ultrasound diagnostic apparatus body. With this, the number of output signal lines from the ultrasound probe 1 can be reduced. In other words, the number of probe cables 11 is reduced.

The control circuit within the probe handle 100 is to control operations of the aforementioned pulsar group 101, preamplifier group 103, and channel control circuit 104. The preamplifier group 103 is configured such that it can individually set up operating conditions such as a bias current, etc. with control signals from this control circuit within the probe handle 100.

The probe handle 10 and the probe connector 12 are connected by the probe cable 11 as described above. The inside of the probe connector 12 is configured with an electronic circuit group 121 consisting of a plurality of electronic circuits, and a control circuit within the probe connector 120. The above electronic circuit group 121 performs additional processing such as amplification, buffering, and adjustment of bandwidth, as necessary, on ultrasound echo signals.

Moreover, the control circuit within the probe connector 120 is for controlling operation of the above electronic circuit group 121 and for generating control signals to be transmitted to the control circuit within the probe handle 100 based on control signals to be transmitted from an ultrasound diagnostic apparatus body 2 described later.

The ultrasound diagnostic apparatus body 2 is configured with a body preamplifier group 240, a body reception delay adding circuit 241, a signal-processing part 25, an image-processing part 26, a display part 27, a body transmission delay circuit 220, a body pulsar group 221, a body control circuit 21, and an operating panel 20.

In the body preamplifier group 240, ultrasound echo signals subjected to first reception delay adding processing are amplified in a group of several channels in the ultrasound probe 1. These amplified ultrasound echo signals are matched for timing in the body reception delay adding circuit 241. The above ultrasound signals are then detected in the signal-processing part 25, and an envelope is extracted.

In addition, after coordinate transformation is performed on this extracted envelope according to a cross-section of the object to be observed O, or appropriate gradation processing, etc. for image display is subjected in the image-processing part 26, it is displayed on the display part 27. With this, form information inside the object to be observed is displayed on the display part 27 in real time as shown in FIG. 11.

Moreover, the body control circuit 21 controls operation of each processing part within the ultrasound diagnostic apparatus body 2, and transmits control information to the control circuit 120 within the probe connector of the probe connector 12. The operating panel 20 is an input part for an operator to perform operation to input or select information in a case in which a continuous wave Doppler mode capable of beam steering is performed, etc. as an operating mode.

Furthermore, the body transmission delay circuit 220 and the body pulsar group 221 are operated when the ultrasound probe does not embed any electronic circuits, i.e., when a regular probe in which an ultrasound diagnostic apparatus body 2 drives an ultrasound vibrator group 102 is connected, and generally, they are configured to be built in the ultrasound diagnostic apparatus body 2, but they are not necessary.

As the operating mode of the ultrasound diagnostic apparatus described above, a continuous wave Doppler (hereinafter referred to as "SCW") mode that is used for measurement of a blood flow rate, etc. is known. The SCW mode divides the ultrasound vibrator group aligned in arrays of N M into a Region B that sends ultrasound and a Region A that receives ultrasound as shown in FIG. 10 to operate, and with this, ultrasound can be continuously sent and received.

At the time of operating in the SCW mode, when transmission and reception of ultrasound of center frequency f0 are performed on blood flow within the object to be observed, the frequency of the ultrasound beams receives Doppler shift frequency fd proportional to the blood flow rate due to the moving blood cell, and ultrasound echoes of f0+fd is received. Therefore, by detecting the Doppler shift frequency fd and by displaying temporal changes, blood flow rate information can be displayed as a Doppler image as shown in FIG. 12.

Moreover, at that time, by mapping two-dimensionally the detected Doppler shift frequency fd, by performing appropriate color transformation, and by displaying it by superimposing over the foregoing ultrasound image, an image inside the object to be observed including the blood flow rate information can be displayed in real time as a color Doppler image (not shown).

In recent years, ultrasound 2D array vibrators have been used for an ultrasound probe, the number of vibrators has increased to several thousands, and the individual size has become very small. In this case, when the probe is directly connected to an ultrasound diagnostic apparatus, because a substantial number of cables is required, the cables as a whole become thick, affecting the operation, and causing difficulty in transmitting high-quality ultrasound echoes that are received by minute vibrators.

Therefore, in the case of ultrasound 2D arrays, etc., the number of signal lines that are input to an ultrasound diagnostic apparatus is often reduced by mounting electronic circuits such as a transmitting circuit and a receiving circuit onto an ultrasound probe, by efficiently amplifying received weak ultrasound echoes, and by performing partial reception beamforming on each unit of several vibrators to be added.

In the SCW mode, in order to amplify extremely weak Doppler signals superimposed on clutter (for example, reflected waves from the cardiac wall) with large amplitude that is detected on ultrasound beams, a wider dynamic range compared to the case of obtaining a normal B mode image is required.

However, the beamformer embedded in the ultrasound probe cannot take a wide dynamic range due to restrictions of electric power to be supplied, etc. This is because it is necessary to supply high electric power to the beamformer in order to secure a sufficient dynamic range; however, an increase of electric power involves heat generation. Because an ultrasound probe is used in contact with a subject, it is necessary to suppress this heat generation, and high electric power cannot be supplied.

Therefore, the conventional ultrasound probe having a reception beamformer cannot truly amplify weak signal components of the SCW due to the abovementioned restriction of the beamformer, and in the case of operating in the SCW mode, output signals cannot be added for each unit of several ultrasound vibrators to output to the ultrasound diagnostic apparatus body. With this, in the conventional ultrasound probe, the number of signal lines within the probe cables connecting the ultrasound probe to the ultrasound diagnostic apparatus body cannot be reduced, and the probe cables had to be made thick.

BRIEF DESCRIPTION OF THE DRAWINGS

FIG. 2A is a diagram for illustrating the operation of the channel control circuit according to the first embodiment.

FIG. 7 is a diagram for illustrating the operation of the channel control circuit according to the Modified Example 2.

DETAILED DESCRIPTION

The present embodiments are to solve the above problem, and the purposes are to secure a wide dynamic range and to reduce the number of signal lines within a probe cable by adding received signals of the same phase for each unit of several ultrasound vibrators to send to an ultrasound diagnostic apparatus body even in an operating mode that divides an ultrasound vibrator group into a region to perform transmission and a region to perform reception as is the case for the SCW mode.

The present embodiments relate to an ultrasound probe having a first ultrasound vibrator group and a second ultrasound vibrator group, and comprise a plurality of matrix switches and an adder. The ultrasound probe according to the present embodiment has a mode to send ultrasound to a predetermined observation point within a subject by the first ultrasound vibrator group, and to receive ultrasound echoes reflected within the subject by the second ultrasound vibrator group.

The plurality of matrix switches extract, based on the distance between the second ultrasound vibrator group and the observation point, a plurality of ultrasound echoes having substantially the same phase from a plurality of ultrasound echoes output by the second ultrasound vibrator group. The adder adds the plurality of ultrasound echoes extracted by the plurality of matrix switches for each of the matrix switches and outputs them.

(First Embodiment)

Figure 9:
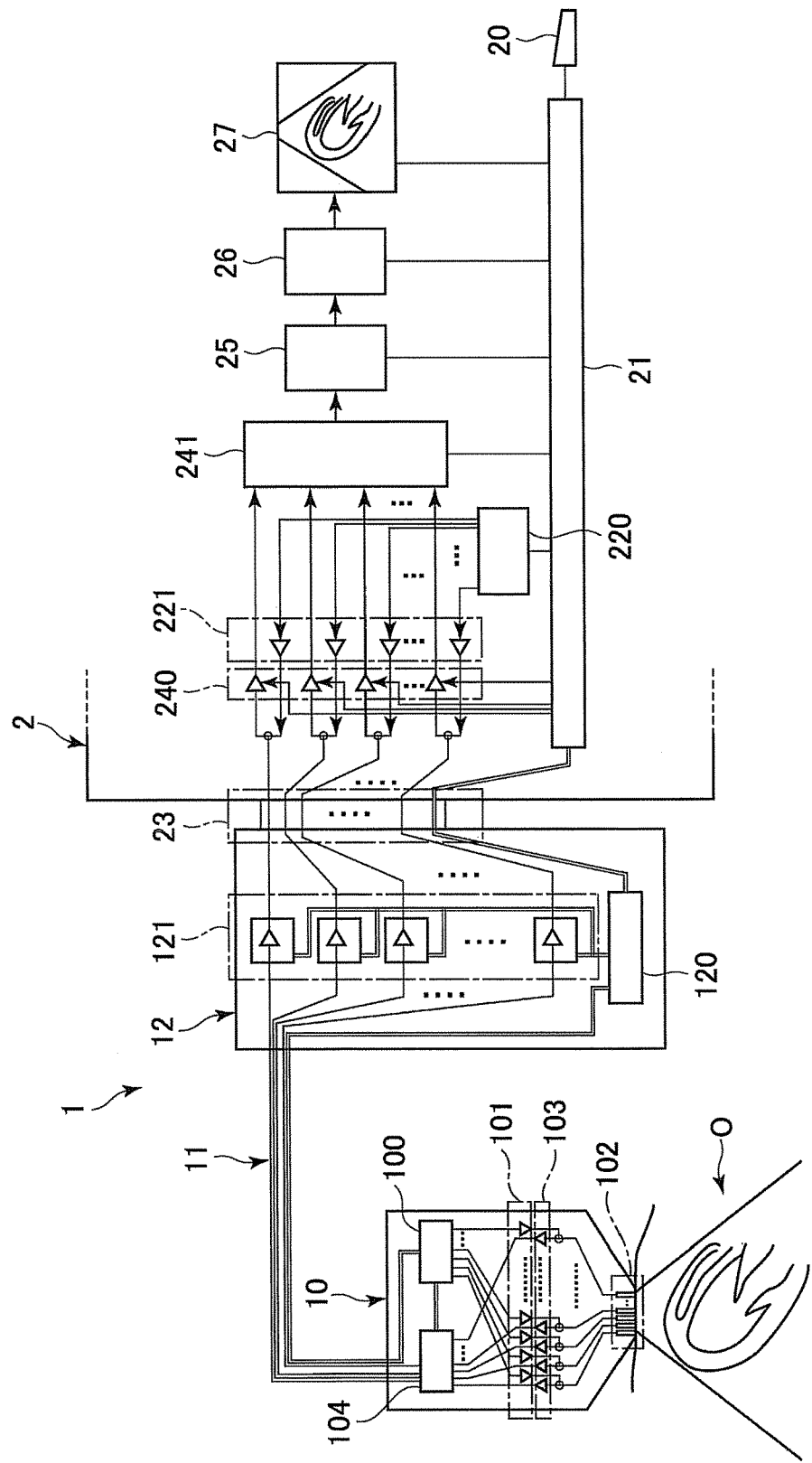
FIG. 9 is a functional block diagram illustrating the configuration of a general ultrasound diagnostic apparatus.

First, the configuration of the ultrasound probe according to the first embodiment is described with reference to FIG. 1. The configuration from a probe connector 12 to an ultrasound diagnostic apparatus body 2 is similar to the configuration of the conventional ultrasound diagnostic apparatus shown in FIG. 9. Here, the configuration of the ultrasound probe 1 is described in detail.

Figure 1:
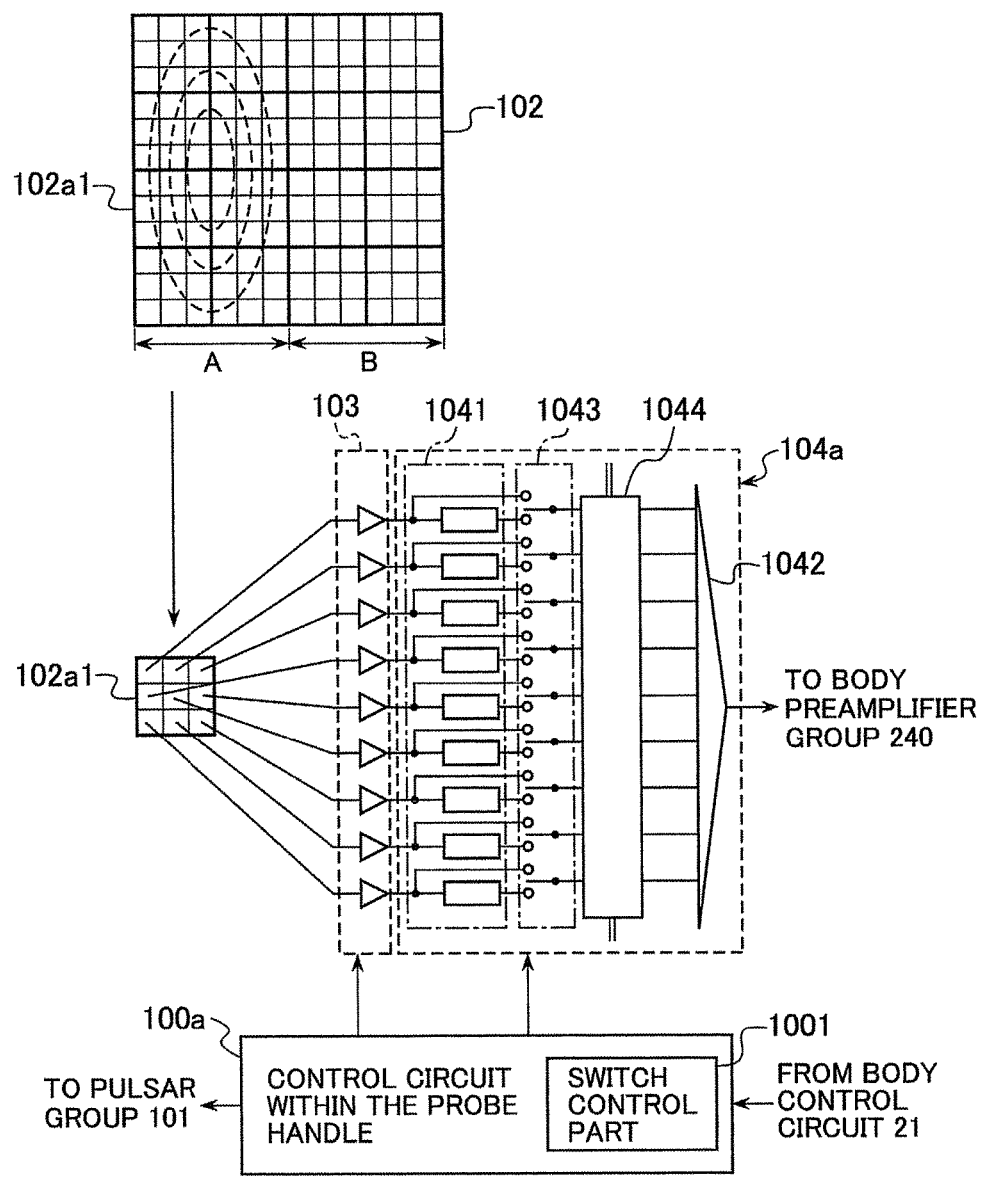
FIG. 1 is a block diagram of a channel control circuit of an ultrasound probe according to the first embodiment.
Figure 10:
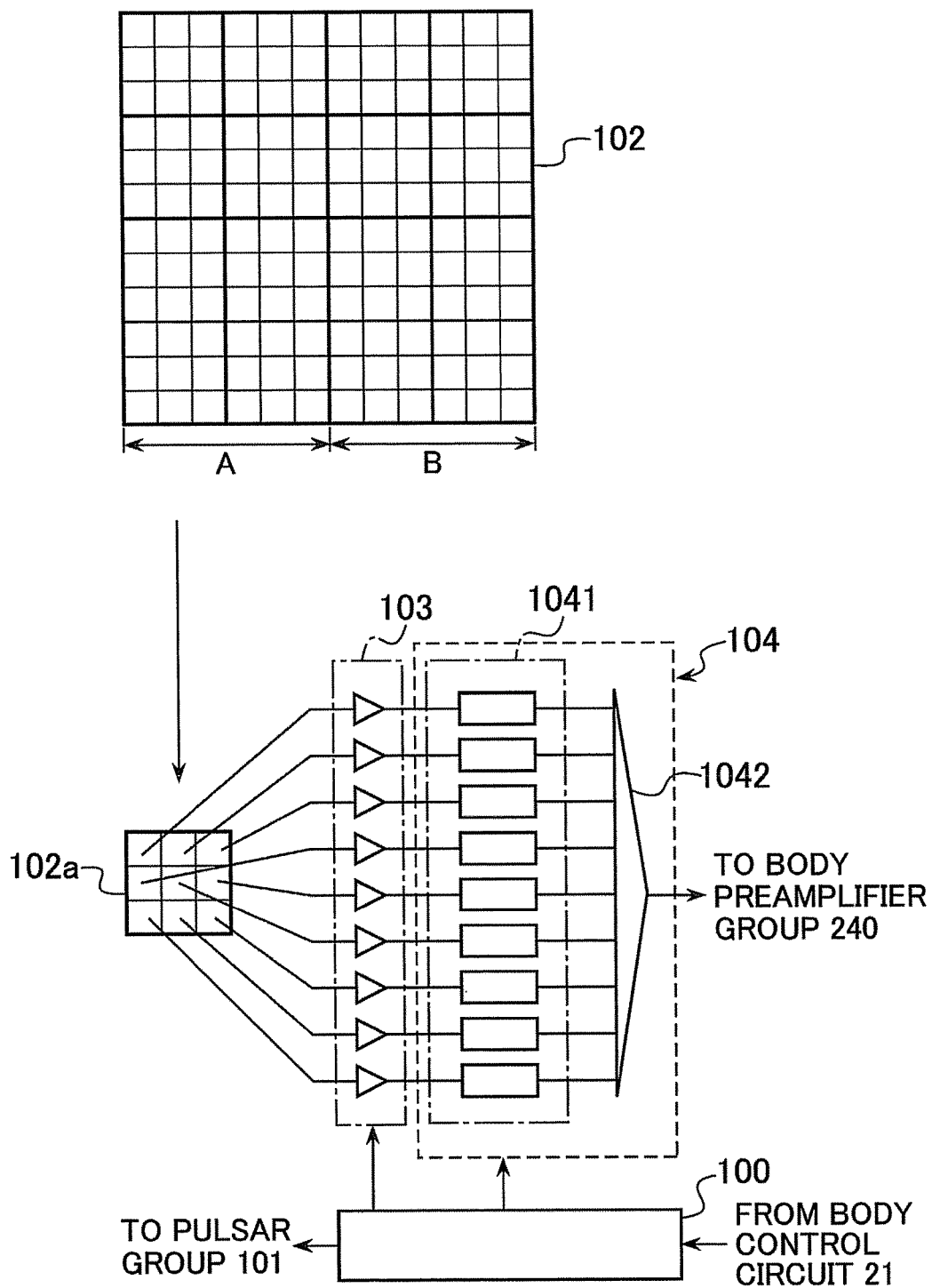
FIG. 10 is a block diagram of a channel control circuit in the conventional ultrasound probe.
Figure 11:
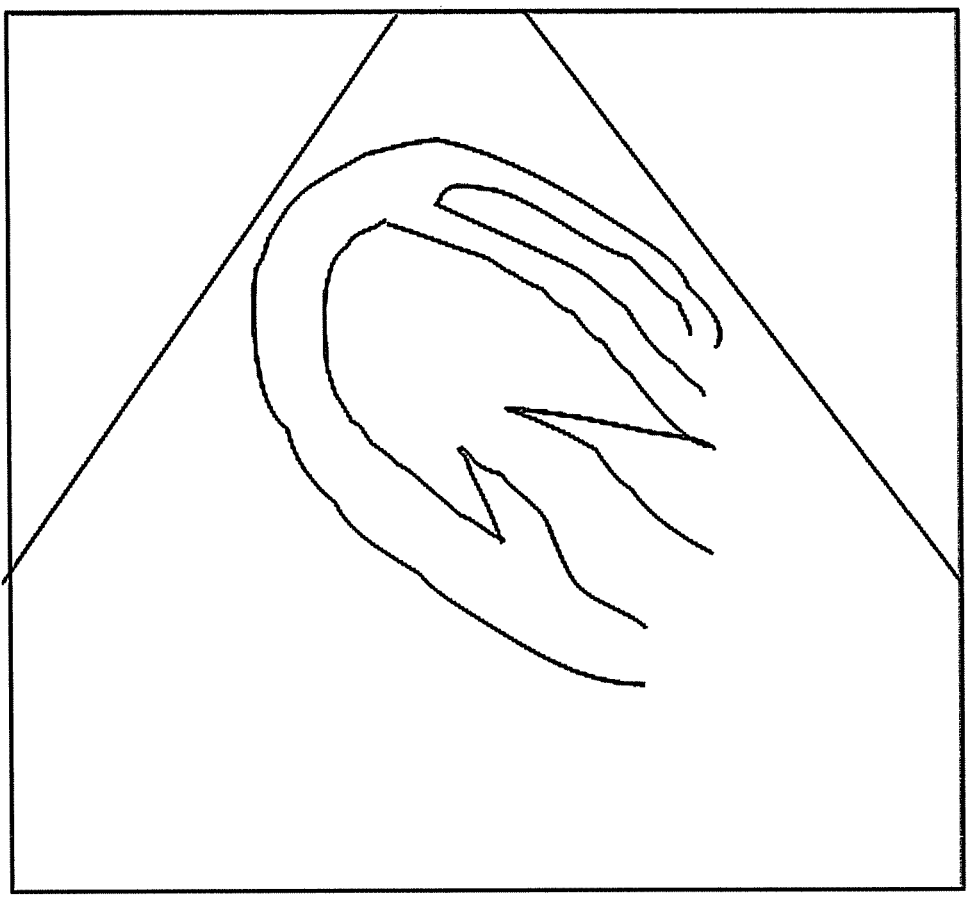
FIG. 11 shows an output example of ultrasound image in the case of B mode.
Figure 12:
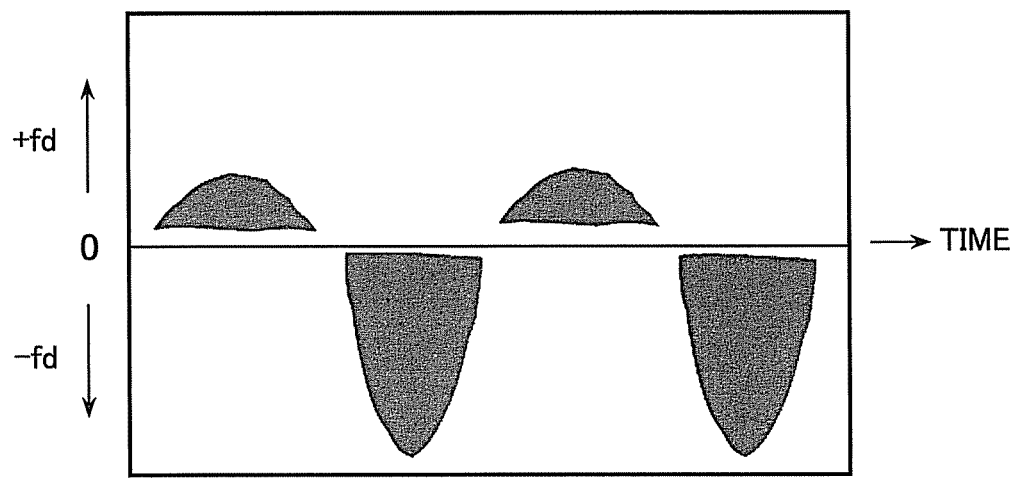
FIG. 12 shows an output example of ultrasound image in the case of SCW mode.

As shown in FIG. 1, a channel control circuit 104*a* according to the present embodiment is characterized by further comprising bypass switches 1043 and matrix switches 1044 in addition to the sub-array reception beamformer group 1041 and the adder 1042. Therefore, in this description, focus is placed on the configuration within a probe handle 10 with a different configuration from that of the conventional ultrasound probe, a body reception delay adding circuit 241 within the ultrasound diagnostic apparatus body 2 that processes transmission signals from the ultrasound probe, and a body control circuit 21 that controls operation of the entire apparatus to describe. Furthermore, components with additional subscripts similar to FIG. 10 show a configuration similar to components given the relevant additional subscripts in FIG. 10.

Firstly, the body control circuit 21 receives a designation of a mode in which the ultrasound diagnostic apparatus operates (hereinafter referred to as "operating mode") by the operator from an operating panel 20, and determines operation of each ultrasound vibrator that configures an ultrasound vibrator group 102.

Specifically, as in the SCW mode, in the case of a mode that divides into a plurality of ultrasound vibrators that send ultrasound and a plurality of ultrasound vibrators that receive ultrasound in order to send and receive ultrasound (hereinafter referred to as "first mode"), the body control circuit 21 divides the ultrasound vibrator group 102 into the Region B that sends ultrasound and the Region A that receives ultrasound.

Moreover, in the case of a mode to both send and receive ultrasound with the same ultrasound vibrators (hereinafter referred to as "second mode") as in the B mode, etc., the body control circuit 21 is set up such that each ultrasound vibrator that configures the ultrasound vibrator group 102 sends and receives ultrasound.

The body control circuit 21 sends and instructs control regarding allocation of the aforementioned ultrasound vibrators to the ultrasound probe 1 as region control signals.

Subsequently, the body control circuit 21 receives setup of an observation point by the operator from the operating panel 20, and calculates transmission delay time and reception delay time of each ultrasound vibrator based on the distance from each ultrasound vibrator that configures the ultrasound vibrator group 102 and the relevant observation point. At this time, in the case of operating in the first mode, the transmission delay time corresponds to each ultrasound vibrator of the Region B that sends ultrasound, and the reception delay time corresponds to each ultrasound vibrator of the Region A that receives ultrasound.

Subsequently, the body control circuit 21 relates reception delay time to each preamplifier of a body preamplifier group 240, and instructs the body reception delay adding circuit 241 to delay processing on each output signal from the relevant preamplifiers. For example, first, the body control circuit 21 relates delay time td1 to signals that output from a preamplifier of the body preamplifier group 240 (hereinafter referred to as "preamplifier of the body") Ch1, and relates delay time td3 to signals output from the preamplifier of the body Ch3. Subsequently, the body control circuit 21 instructs, in accordance with the relevant relations, the body reception delay adding circuit 241 to perform delay processing on each of them (the body reception delay adding circuit 241 is described later).

Moreover, the body control circuit 21 creates matrix switch switching signals that control the matrix switch 1044 included in the ultrasound probe 1 such that signals having the related delay time are input to each preamplifier (for example, preamplifiers Ch1 to Ch3) of the body preamplifier group 240 (the matrix switch 1044 is described later).

The body control circuit 21 sends the calculated transmission delay time and reception delay time, the operating mode, the region control signals, and the matrix switch switching signals as probe control data to a control circuit within the probe handle 100*a* via a control circuit within the probe connector 120 (the control circuit within the probe handle 100*a* is described later).

The channel control circuit 104*a* according to the present embodiment is configured with a sub-array reception beamformer group 1041, bypass switches 1043, matrix switches 1044, and an adder 1042, as shown in FIG. 1.

The sub-array reception beamformer group 1041 is a delay circuit that performs, with a plurality of preamplifiers included in a preamplifier group 103 as one group, delay processing so as to match phase difference of output signals from the preamplifiers included in the relevant group to output them.

In the ultrasound probe 1 according to the present embodiment, a signal line that is brought out from the input side of the sub-array reception beamformer group 1041 and that bypasses the sub-array reception beamformer group 1041 (hereinafter referred to as "bypass signal line") is provided. Output signals from the preamplifier group 103 are switched by the bypass switch 1043 so as to pass through either the sub-array reception beamformer group 1041 or the bypass signal line.

The bypass switch 1043 is provided on the output side of the sub-array reception beamformer group 1041, and is configured switchably between a first contact point provided on the output side of the sub-array reception beamformer group 1041 and a second contact point provided on the bypass signal line side.

The bypass switch 1043 is switched by a mode in which the ultrasound diagnostic apparatus operates (hereinafter referred to as "operating mode") by the switch control part 1001 (the switch control part 1001 is described later). This bypass switch 1043 is equivalent to a switching part.

Specifically, as in the SCW mode, in the case of a mode that divides into a plurality of ultrasound vibrators that send ultrasound and a plurality of ultrasound vibrators that receive ultrasound in order to send and receive ultrasound (hereinafter referred to as "first mode"), it is switched to the second contact point, and delay processing by the sub-array reception beamformer group 1041 is not performed on the output signals from the preamplifier group 103.

Moreover, in the case of a mode to both send and receive ultrasound with the same ultrasound vibrators (hereinafter referred to as "second mode") as in the B mode, etc., it is switched to the first contact point, the output signals from the preamplifier group 103 are input to the sub-array reception beamformer group 1041, and delay processing is performed in a conventional manner.

The adder 1042 reduces the number of output signal lines from the ultrasound probe 1 by adding and outputting signals output from the plurality of bypass switches 1043. The adder 1042 is provided, for example, so as to add signals output from a predetermined sub-array (for example, sub-array 102a1) configured with the plurality of ultrasound vibrators via each preamplifier of the preamplifier group 103 and the bypass switch 1043 (hereinafter, this signal may be referred to as "signal output from a sub-array").

The signals output from the adder 1042 are input to the body preamplifier group 240 via a probe cable 11 and an electronic circuit group 121. The adder 1042 and each preamplifier of the body preamplifier group 240 correspond on a one-to-one basis, and signals output from a predetermined adder 1042 (for example, adder 1042a1) are input to a predetermined preamplifier (for example, preamplifier Ch1 of the body preamplifier group 240).

The matrix switch 1044 intervenes between the bypass switch 1043 and the adder 1042, and outputs signals input from the bypass switch 1043 to the adder 1042. At this time, the matrix switch 1044 is controlled by the switch control part 1001 so as to switch adders to which each signal input from the bypass switch 1043 is output according to the operating mode (the first mode or the second mode) (the switch control part 1001 is described later).

Between each matrix switch 1044, the input signals are configured to be transferable. With this, it becomes possible to output the signals input in a predetermined matrix switch (for example, matrix switch 1044a1) to an adder (for example, adder 1042b1) provided on the output side of a different matrix switch (for example, matrix switch 1044b1). Furthermore, this operation is controlled by the switch control part 1001.

When the ultrasound probe 1 operates in the second mode, the matrix switch 1044 is controlled by the switch control part 1001 so as to output the signals input from the bypass switch 1043, to the adder 1042 placed on the output side. Moreover, when the ultrasound probe 1 operates in the first mode, the matrix switch 1044 is controlled by the switch control part 1001 so as to output the input signals to the predetermined adder 1042 for each of their phases. This control is described later along with the operation of the switch control part 1001.

The control circuit within the probe handle 100a according to the present invention is provided with the switch control part 1001.

The control circuit within the probe handle 100a instructs, based on the transmission delay time included in the probe control data received from the body control circuit 21, a pulsar group 101 corresponding to ultrasound vibrators that send ultrasound (for example, ultrasound vibrators included in the Region B in the case of the first mode) to send ultrasound. Moreover, the control circuit within the probe handle 100a sends, to the switch control part 1001, the operating mode, the reception delay time, and the matrix switch switching signals included in the probe control data received from the body control circuit 21, and instructs switching of the bypass switch 1043 and the matrix switch 1044.

The switch control part 1001 switches the bypass switch 1043 according to the received operating mode. Moreover, the switch control part 1001 controls the sub-array reception beamformer group 1041 and the matrix switch 1044 based on the reception delay time of each ultrasound vibrator and the matrix switch switching signals received.

Figure 2B:
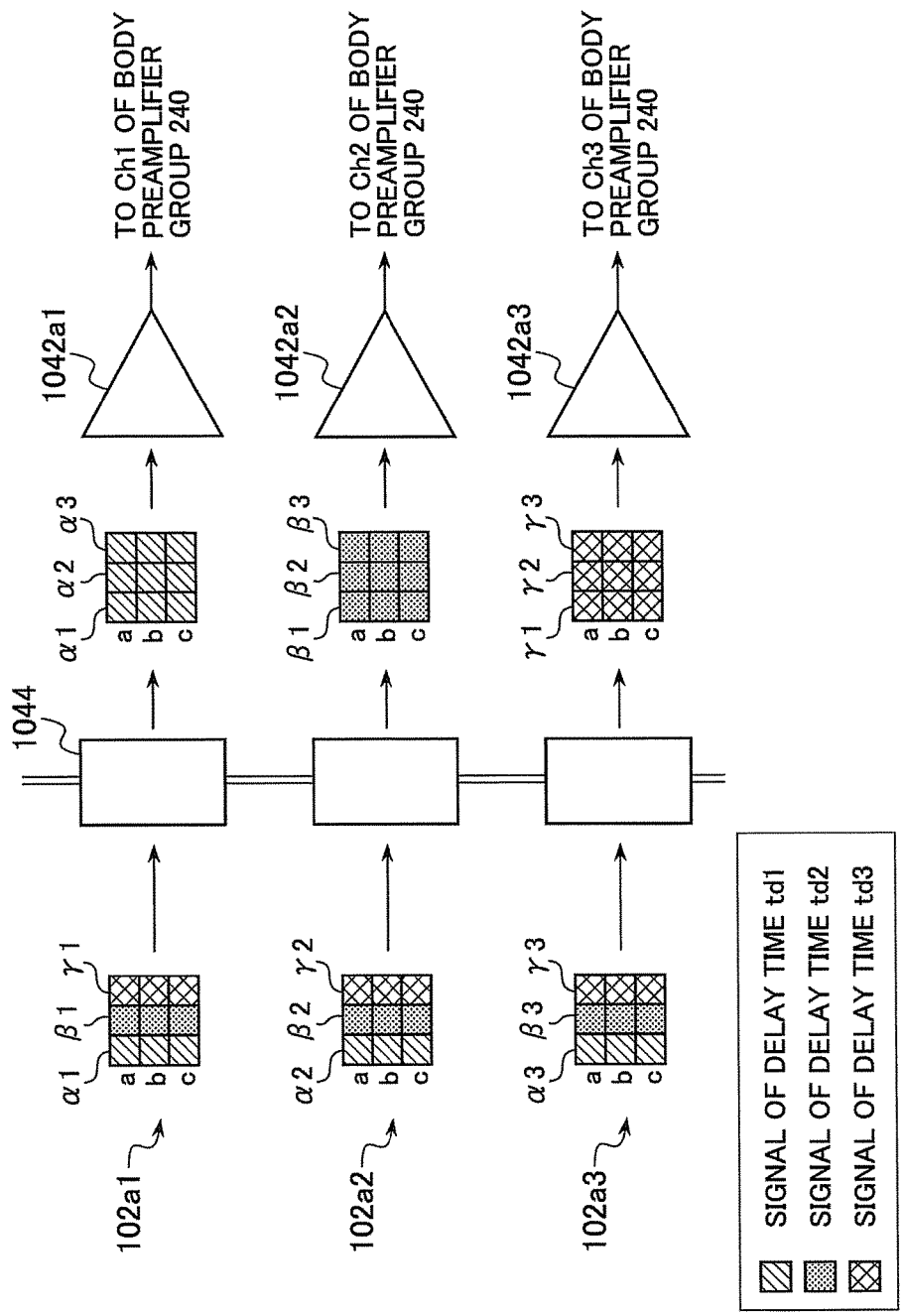
FIG. 2B is a diagram for illustrating the operation of the channel control circuit according to the first embodiment.

The controls of the sub-array reception beamformer group 1041, the bypass switch 1043, and the matrix switch 1044 by the switch control part 1001 are described in detail for each operating mode with reference to FIG. 1, FIG. 2A, and FIG. 2B.

First, the operation when the ultrasound probe 1 operates in the second mode (for example, the B mode) is described with reference to FIG. 2A. FIG. 2A is a diagram for illustrating the operation of the channel control circuit 104a in the case in which the ultrasound probe 1 operates in the second mode.

When the switch control part 1001 operates in the second mode, it switches the bypass switch 1043 to the first contact point such that signals from each preamplifier of the preamplifier group 103 pass through the sub-array reception beamformer group 1041. At this time, the switch control part 1001 sends simultaneously, to each sub-array reception beamformer, the reception delay time corresponding to ultrasound vibrators that are the output source of the signals that are input to each sub-array reception beamformer configuring the sub-array reception beamformer group 1041, and instructs delay processing. This rectifies, the phases of signals from ultrasound vibrators corresponding to, for example, α1 row, β1 row, and γ1 row of a sub-array 102a1 to signals of the delay time td1.

Subsequently, the switch control part 1001, based on the reception delay time and the matrix switch switching signals, controls the matrix switch 1044 such that the signals output from the sub-array reception beamformer group 1041 and input to the matrix switch 1044 via the bypass switch 1043 are output to the adder 1042 provided on the output side of the relevant matrix switch 1044.

Specifically, the switch control part 1001, as shown in FIG. 2A, controls the matrix switch 1044 such that signals from the ultrasound vibrators corresponding to, for example, α1 row, β1 row, and γ1 row of the sub-array 102a1 are output to an adder 1042a1 corresponding to the relevant sub-array 102a1. Similarly, signals from the ultrasound vibrators corresponding to α3 row, β3 row, and γ3 row of a sub-array 102a3 are output to an adder 1042a3 corresponding to the relevant sub-array 102a3.

Therefore, when the ultrasound probe 1 operates in the second mode, the channel control circuit 104a has a configuration to perform the same operation as the conventional channel control circuit 104 shown in FIG. 10.

Subsequently, the operation when the ultrasound probe 1 operates in the first mode (for example, the SCW mode) is described with reference to FIG. 2B. FIG. 2B is a diagram for illustrating the operation of the channel control circuit 104a in the case in which the ultrasound probe 1 operates in the first mode.

When the switch control part 1001 operates in the first mode, it switches the bypass switch 1043 to the second contact point such that signals from each preamplifier of the preamplifier group 103 pass through the bypass signal line. With this, in the case of operating in the first mode, the sub-array reception beamformer group 1041 is bypassed, and delay processing is not performed on the signals from each ultrasound vibrator.

Subsequently, the switch control part 1001, based on the reception delay time and the matrix switch switching signal, controls the matrix switch 1044 such that among the signals output from each ultrasound vibrator via the preamplifier group 103, the signals of a predetermined phase (for example, signals of delay time td1) are output to the predetermined adder 1042 (e.g., adder 1042a1).

For example, in FIG. 2B, signals from ultrasound vibrators corresponding to α1 row of the sub-array 102a1, α2 row of the sub-array 102a2, and α3 row of the sub-array 102a3 have the same phase (delay time td1). Similarly, signals from ultrasound vibrators corresponding to β1 row, β2 row, and β3 row have the same phase (delay time td2), and signals from ultrasound vibrators corresponding to γ1 row, γ2 row, and γ3 row have the same phase (delay time td3).

At this time, the switch control part 1001, as shown in FIG. 2B, controls the matrix switch 1044 such that the signals from ultrasound vibrators corresponding to α1 row of the sub-array 102a1, α2 row of the sub-array 102a2, and α3 row of the sub-array 102a3 that have the same phase (delay time td1) are output to the adder 1042a1 related to the delay time td1 by the matrix switch switching signals. Similarly, the switch control part 1001 controls the matrix switch 1044 such that the signals from ultrasound vibrators corresponding to β1 row, β2 row, and β3 row are output to the adder 1042a2 related to the delay time td2, and the signals from ultrasound vibrators corresponding to γ1 row, γ2 row, and γ3 row are output to the adder 1042a3 related to the delay time td3.

Furthermore, in the above, the matrix switch 1044 has been described as being provided for each adder 1042 that adds signals output from a predetermined sub-array (for example, sub-array 102a1) as shown in FIG. 1; however, one matrix switch 1044 may be provided for the plurality of adders 1042.

The signals output from the adder 1042 are amplified by the body preamplifier group 240 via the probe cable 11 and the electronic circuit group 121. As shown in FIG. 2A and FIG. 2B, each adder 1042 within the ultrasound probe 1 and each preamplifier of the body preamplifier group 240 are related on a one-to-one basis by matrix switch switching signals. Therefore, for example, the signals output from the adder 1042a1 are output to the preamplifier Ch1, and the signals output from the adder 1042a3 are output to the preamplifier Ch3.

Based on the above, each adder (for example, adders 1042a1 to 1042a3) within the ultrasound probe 1 and each preamplifier (for example, preamplifiers Ch1 to Ch3) of the body preamplifier group 240 are related to each other.

The signals amplified in the body preamplifier group 240 and output are output to the signal-processing part 25 after they are input to the body reception delay adding circuit 241, subjected to delay processing, and added. At this time, the body reception delay adding circuit 241 performs, in accordance with control from the body control circuit 21, delay processing on each signal input from each preamplifier included in the body preamplifier group 240 (the body control circuit 21 is described later).

Specifically, signals of a predetermined phase are input from each preamplifier included in the body preamplifier group 240 by control of the matrix switch 1044 based on the matrix switch switching signals; hence, delay time corresponding to the relevant phase is given to each of the relevant preamplifier. For example, as shown in FIG. 2B, signals from the adder 1042a1 are input to the preamplifier Ch1 of the body preamplifier group 240. Therefore, delay processing is performed on the signals from the preamplifier Ch1 based on the reception delay time for ultrasound vibrators corresponding to α1 row of the sub-array 102a1, α2 row of the sub-array 102a2, and α3 row of the sub-array 102a3.

(Processing)

Figure 3:
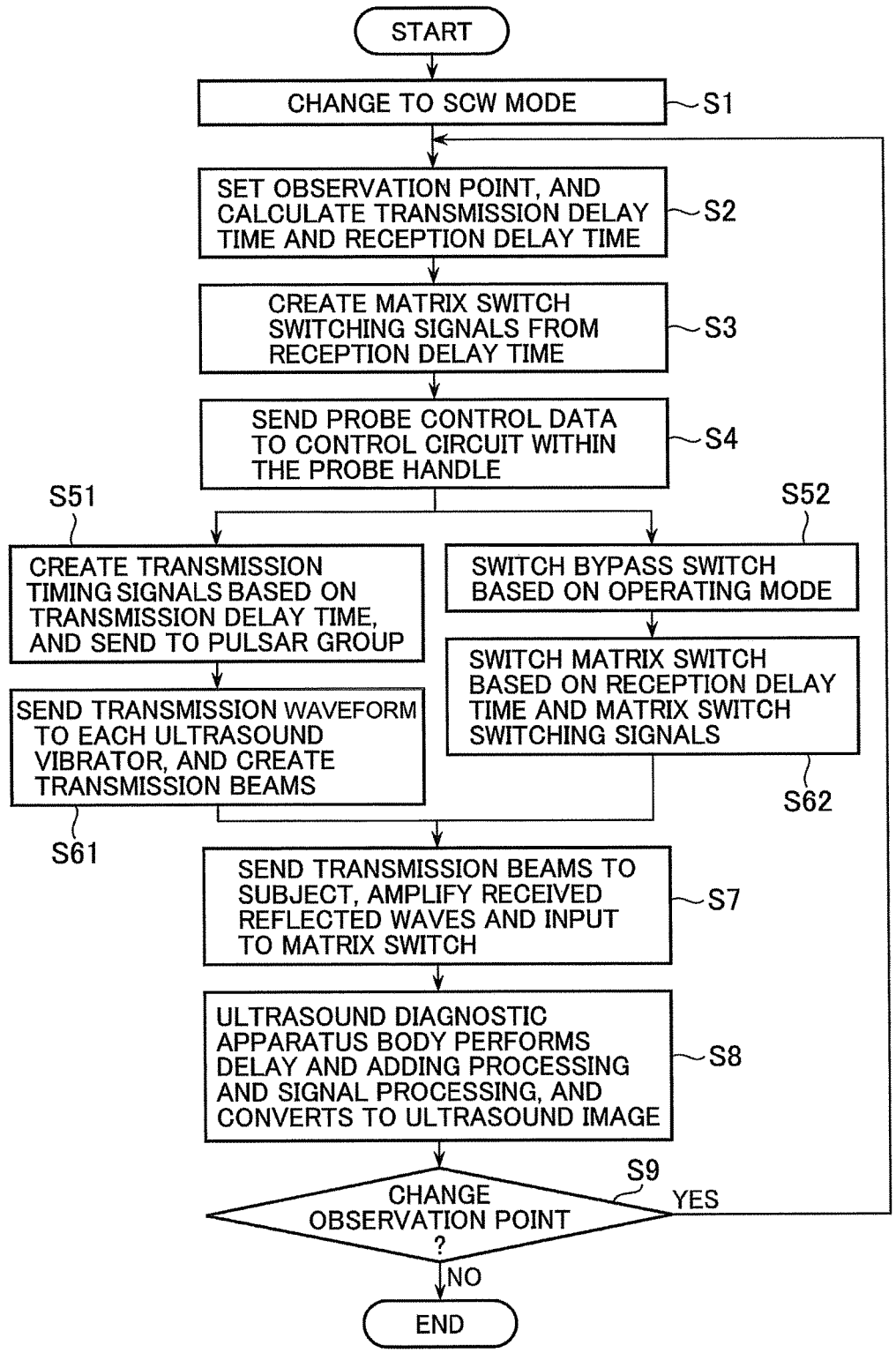
FIG. 3 is a flowchart illustrating the operation of the ultrasound probe according to the first embodiment.

Subsequently, the operation in the first mode of the ultrasound probe 1 according to the present embodiment is described with reference to FIG. 3. FIG. 3 is a flowchart illustrating the operation of the ultrasound probe according to the present embodiment.

(Step S1)

First, the body control circuit 21 receives a designation by the operator from the operating panel 20, and changes the operating mode of the ultrasound diagnostic apparatus to the SCW mode. At this time, region control signals that divide the ultrasound vibrator group 102 into the Region A that receives ultrasound and the Region B that sends ultrasound are also created.

(Step S2)

Subsequently, the body control circuit 21 receives a designation of an observation point by the operator from the operating panel 20, and calculates transmission delay time corresponding to each ultrasound vibrator of the Region B that sends ultrasound and reception delay time corresponding to each ultrasound vibrator of the Region A that receives ultrasound based on the distance between each ultrasound vibrator that configures the ultrasound vibrator group 102 and the observation point.

(Step S3)

Once the reception delay time corresponding to each ultrasound vibrator of the Region A that receives ultrasound is calculated, the body control circuit 21 relates reception delay time (for example, td1 to td3) to each preamplifier of the body preamplifier group 240 (for example, preamplifiers Ch1 to Ch3), and creates matrix switch switching signals that control the matrix switch 1044 included in the ultrasound probe 1 such that signals having the related delay time are input to each preamplifier of the body preamplifier group 240.

(Step S4)

Subsequently, the body control circuit 21 sends the calculated transmission delay time and reception delay time, the region control signals, the operating mode, and the matrix switch switching signals as probe control data to the control circuit within the probe handle 100a via the control circuit within the probe connector 120. Once the control circuit within the probe handle 100a receives the probe control data from the body control circuit 21, it first divides the ultrasound vibrator group 102 into the Region A that receives ultrasound and the Region B that sends ultrasound based on the region control signals within the probe control data.

(Step S51)

Subsequently, the control circuit within the probe handle 100a creates transmission timing signals based on the transmission delay time within the probe control data, and sends to the pulsar group 101.

(Step S61)

The pulsar group 101 sends the transmission waveform to each ultrasound vibrator of the ultrasound vibrator group 102 based on the transmission timing signals received from the control circuit within the probe handle 100a, and creates transmission beams. Furthermore, the processing according to Step S51 and Step S61 are similar to the conventional techniques.

(Step S52)

The control circuit within the probe handle 100a instructs the switch control part 1001 to switch the bypass switch 1043 based on the operating mode within the probe control data along with the processing according to Step S51 and Step S61. The switch control part 1001 switches the bypass switch 1043 to the bypass signal line side based on the operating mode (the first operating mode in this case).

(Step S62)

Moreover, the control circuit within the probe handle 100a instructs the switch control part 1001 to switch the matrix switch 1044 based on the reception delay time and the matrix switch switching signals within the probe control data. The switch control part 1001 switches the matrix switch 1044 based on the reception delay time and the matrix switch switching signals such that among the signals output from each ultrasound vibrator via the preamplifier group 103, the signals having the same phase are output to the predetermined adder 1042.

(Step S7)

Subsequently, the transmission beams are sent from each ultrasound vibrator of the Region B that sends ultrasound, and reflected waves thereof are received by ultrasound vibrators corresponding to the Region A that receives ultrasound. The ultrasound echo signals received by the ultrasound vibrators of the Region A are amplified in the preamplifier group 103, pass through the bypass signal line side by switching of the bypass switch 1043, and are input to the matrix switch 1044.

At this time, as shown in FIG. 2B, the signals having the same phase (for example, signals output from ultrasound vibrators corresponding to $\alpha 1$ row, $\alpha 2$ row, and $\alpha 3$ row) are output to the adder 1042 (for example, adder 1042$a$1) related to the signals of a predetermined phase (for example, signals of delay time td1) by switching of the matrix switch 1044, and the signals that have been added by the relevant adder 1042 are output to a preamplifier of the body related to the relevant adder (for example, preamplifier Ch1 of the body) by the matrix switch switching signals via the electronic circuit group 121.

(Step S8)

The body preamplifier group 240 amplifies the received signals and inputs to the body reception delay adding circuit 241. At this time, the body control circuit 21 relates the reception delay time to each preamplifier of the body preamplifier group 240 in response to the control of the matrix switch 1044, and instructs delay processing to the body reception delay adding circuit 241. The body reception delay adding circuit 241 performs delay processing on the signals from each preamplifier in accordance with the instruction from the body control circuit 21, and outputs to the signal-processing part 25 after adding.

The signals output from the body reception delay adding circuit 241 are converted to an ultrasound image in the image-processing part 26 after being subjected to signal processing in the signal-processing part 25, and are displayed on the display part 27.

(Step S9)

Subsequently, when a change of the observation point is instructed by the operator from the operating panel 20 (Step S9, Y), transmission delay time and reception delay time are calculated again for the newly designated observation point, and the processing on the new observation point is executed. When there is no instruction regarding change of the observation point (Step S9, N), the processing is terminated.

According to the ultrasound probe according to the first embodiment, in the ultrasound diagnostic apparatus using an ultrasound 2D array probe embedding electronic circuits such as a preamplifier group, a wide dynamic range can be secured without being limited by restriction on the performance of the electronic circuits (sub-array reception beamformer group 1041) embedded in the probe. With this, reception performance can be secured in the first mode as well (mode that divides into a plurality of ultrasound vibrators that send ultrasound and a plurality of ultrasound vibrators that receive ultrasound in order to send and receive ultrasound) such as the SCW mode.

Moreover, in the case in which a wide dynamic range is required as in the first mode as well, it becomes possible to add received signals for each unit of several vibrators and send to the ultrasound diagnostic apparatus body; therefore, it becomes possible to reduce the number of signal lines within a probe cable, making it possible to make the probe cable to be thinner than a conventional cable.

(Modified Example 1)

Figure 4:
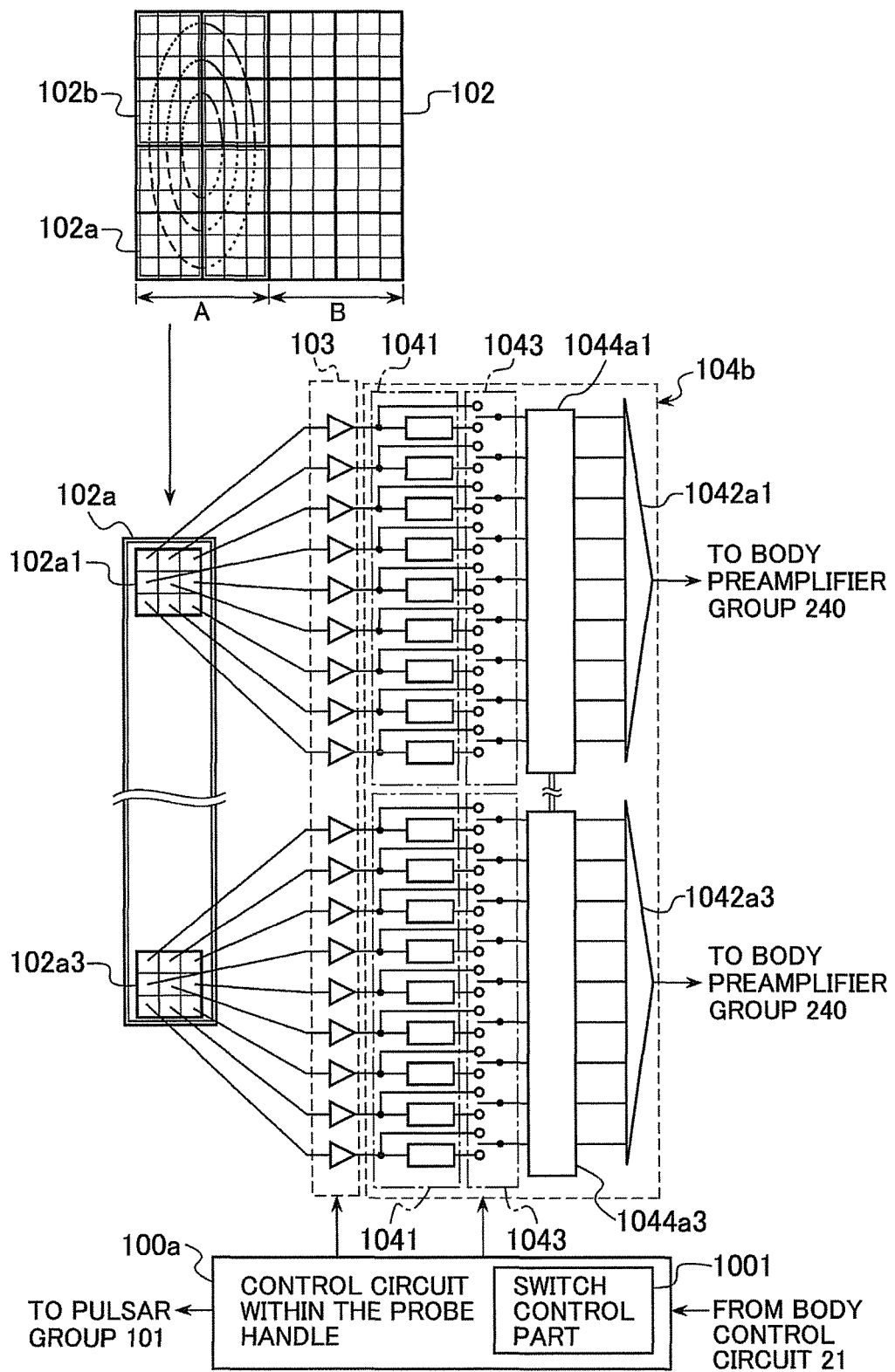
FIG. 4 is a block diagram of a channel control circuit of an ultrasound probe according to the Modified Example 1.

Subsequently, the configuration of an ultrasound probe according to the Modified Example 1 is described with reference to FIG. 4 and FIG. 5. FIG. 4 is a block diagram of a channel control circuit 104$b$ in the ultrasound probe according to the Modified Example 1.

Figure 5:
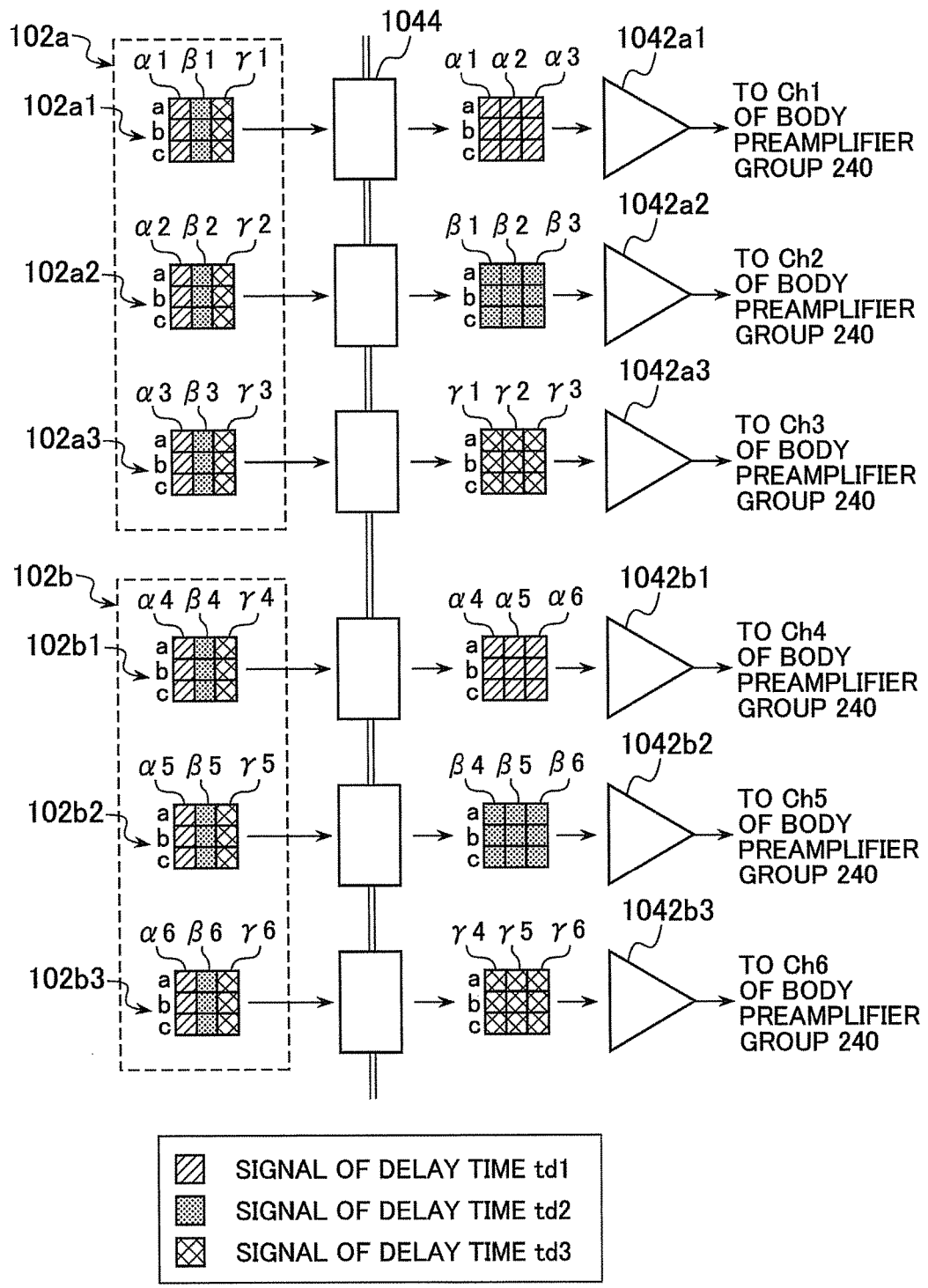
FIG. 5 is a diagram for illustrating the operation of the channel control circuit according to the Modified Example 1.

Moreover, FIG. 5 is a diagram for illustrating the operation of the channel control circuit 104$b$ according to the Modified Example 1.

Furthermore, in description of the ultrasound probe according to the Modified Example 1, focus is placed on an operation in the first mode of the switch control part 1001 and the matrix switch 1044, which are different from the ultrasound probe according to the first embodiment, to describe (the operation in the second mode is similar to the first embodiment).

The matrix switch 1044 according to the first embodiment extracts signals having the same phase from all ultrasound vibrators included in the Region A of the ultrasound vibrator group 102, and controls so as to output them to the predetermined adder 1042.

Therefore, it is necessary for each matrix switch to extract the signals with reference to all ultrasound vibrators included in the Region A of the ultrasound vibrator group 102, and the processing of each matrix switch becomes complicated.

In the ultrasound probe according to the Modified Example 1, as shown in FIG. 4, the ultrasound vibrator group 102 is divided into subgroups (for example, subgroups 102$a$ and 102$b$) configured with two or more sub-arrays (for example, sub-arrays 102$a$1 to 102$a$3), and each matrix switch 1044 extracts signals having the same phase from the ultrasound vibrators included in the corresponding subgroup. With this, each matrix switch 1044 only needs to refer to the ultrasound vibrators included in the subgroup, and it becomes possible to reduce the processing of each matrix switch 1044. The ultrasound probe according to the Modified Example 1 is described in detail below.

Furthermore, in describing the ultrasound probe according to the Modified Example 1, in the examples of FIG. 4 and FIG. 5, sub-arrays 102$a$1 to 102$a$3 are included in a subgroup 102$a$, and sub-arrays 102$b$1 to 102$b$3 are included in a subgroup 102$b$. Moreover, in the example of FIG. 5, the ultrasound vibrators corresponding to $\alpha 1$ row to $\alpha 3$ row of the sub-arrays 102$a$1 to 102$a$3 and $\alpha 4$ row to $\alpha 6$ row of the sub-arrays 102$b$1 to 102$b$3 output signals having the same phase (delay time td1).

Similarly, ultrasound vibrators corresponding to $\beta 1$ row to $\beta 3$ row of the sub-arrays 102$a$1 to 102$a$3 and $\beta 4$ row to $\beta 6$ row of the sub-arrays 102$b$1 to 102$b$3 have the same phase (delay time td2), and ultrasound vibrators corresponding to $\gamma 1$ row to $\gamma 3$ row of the sub-arrays 102$a$1 to 102$a$3 and $\gamma 4$ row to $\gamma 6$ row of the sub-arrays 102$b$1 to 102$b$3 have the same phase (delay time td3).

The switch control part 1001 according to the Modified Example 1, when the operating mode is the first mode (for example, the SCW mode), controls the matrix switch 1044 such that signals having the predetermined same phase (for example, delay time td1) within the same subgroup (for example, signals from the ultrasound vibrators corresponding to $\alpha 1$ row, $\alpha 2$ row, and $\alpha 3$ row) are input to an adder related to the relevant phase within the relevant subgroup (for example, adder 1042a1) as shown in FIG. 5.

At this time, the switch control part 1001 does not perform transfer of signals to the adders 1042 included in different subgroups.

Specifically, the switch control part 1001 as shown in FIG. 5 controls such that the signals from the ultrasound vibrators included in the subgroup 102a are input to the adders 1042a1 to 1042a3 related to the relevant subgroup 102a. At this time, the signals from the ultrasound vibrators included in the subgroup 102a are not input to the adders 1042b1 to 1042b3 related to other subgroups such as the subgroup 102b.

In other words, to describe the ultrasound vibrators corresponding to α1 row to α3 row of the sub-arrays 102a1 to 102a3 and α4 row to α6 row of the sub-arrays 102b1 to 102b3 from which the signals of delay time td1 are output as an example, the signals from the ultrasound vibrators corresponding to α1 row to α3 row of the sub-arrays 102a1 to 102a3 are output to the adder 1042a1, and the signals from the ultrasound vibrators corresponding to α4 row to α6 row of the sub-arrays 102b1 to 102b3 are input to the adder 1042b1.

Furthermore, in the above description, the example in which the switch control part 1001 performs relating between subgroups and adders has been described; however, the body control circuit 21 may perform relating between subgroups and adders. In this case, the body control circuit 21 sends to the ultrasound probe 1 as matrix switch switching signals also including control information regarding the relating between subgroups and adders.

Based on the above, based on the ultrasound probe according to the Modified Example 1, each matrix switch 1044 only needs to refer to the ultrasound vibrators included in the related subgroup, and it is possible to reduce the processing of each matrix switch 1044.

(Modified Example 2)

Figure 6:
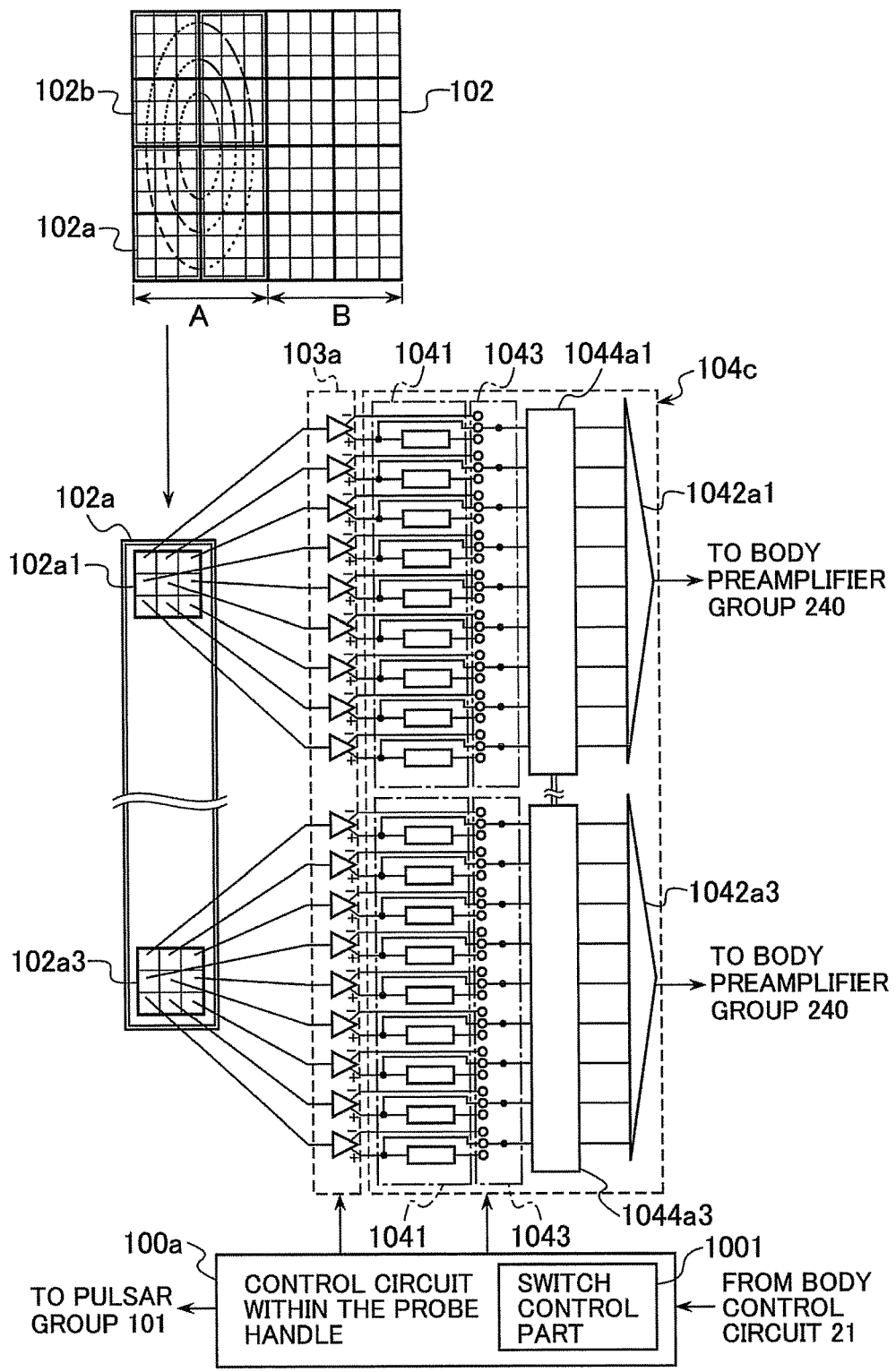
FIG. 6 is a block diagram of a channel control circuit of an ultrasound probe according to the Modified Example 2.

Subsequently, the configuration of an ultrasound probe according to the Modified Example 2 is described with reference to FIG. 6. FIG. 6 is a block diagram of a channel control circuit 104c in the ultrasound probe according to the Modified Example 2.

Furthermore, in the description of the ultrasound probe according to the Modified Example 2, focus is placed on the configuration of the preamplifier group 103 and the bypass switch 1043, and the operation in the first mode of the switch control part 1001 and the matrix switch 1044 that are different from the ultrasound probes according to the first embodiment and the Modified Example 1 to describe (the operation in the second mode is similar to the first embodiment).

In the ultrasound probes according to the first embodiment and the Modified Example 1, due to the configuration of the channel control circuits 104a and 104b, the types of phases that can be set to each vibrator of the Region A that receives ultrasound are limited by the number of signal lines that are input to each adder and the number of adders. For example, as with the operation of the channel control circuit 104a according to the first embodiment shown in FIG. 2B, description is given as if the signals from the ultrasound vibrators included in the sub-arrays 102a1 to 102a3 are input to the adders 1042a1 to 1042a3. In this case, the types of phases that can be set are three at maximum, which is the number of the adders. Moreover, the number of signal lines that can be input to each adder is nine at maximum; therefore, when there are ten signals or more that have the same phase, the types of phases that can be set becomes less than the number of the adders (less than three types).

In the ultrasound probe according to the Modified Example 2, as shown in FIG. 6, it becomes possible to invert the phases of some signals 180 degrees by each preamplifier of the preamplifier group 103. With this, with the wavelength of signals as 2T for example, by inverting the phase of signals that are output with delay of td+T, it is possible to add to signals that are output with delay of td in order to output, and it becomes possible to reduce the aforementioned restriction regarding the types of phases that can be set. The ultrasound probe according to the Modified Example 2 is described in detail below.

Each preamplifier configuring the preamplifier group 103 according to the Modified Example 2 is configured to be able to receive an instruction from the switch control part 1001, invert the phase of input signals 180 degrees, and output them. The preamplifier group 103 is provided with a signal line (this signal line is referred to as an "inverted signal line"), which is different from a signal line that outputs signals whose phase is not inverted, and it outputs signals whose phase has been inverted to the relevant inverted signal line.

The bypass switch 1043 according to the Modified Example 2 is configured to be switchable to either the first contact point provided on the output side of the sub-array reception beamformer group 1041, the second contact point provided on the bypass signal line side, or the third contact point provided in the abovementioned inverted signal line.

Here, with reference to FIG. 7, the operation of the switch control part 1001 and matrix switch 1044 according to the Modified Example 2 is described. FIG. 7 is a diagram for illustrating the operation of the channel control circuit 104c according to the Modified Example 2.

Furthermore, in describing the ultrasound probe according to the Modified Example 2, in the examples of FIG. 6 and FIG. 7, the sub-arrays 102a1 to 102a3 are included in the subgroup 102a, and the sub-arrays 102b1 to 102b3 are included in the subgroup 102b.

Moreover, in the example of FIG. 7, the ultrasound vibrators corresponding to α1 row of the sub-array 102a1 and α3 row of the sub-array 102a3 output signals having the same phase (delay time td1) and ultrasound vibrators corresponding to α2' row of the sub-array 102a2 output signals in which the phase is inverted 180 degrees (delay time td1+T) relative to the signals output by the ultrasound vibrators corresponding to α1 row and α3 row. Similarly, the ultrasound vibrators corresponding to β1 row and β3 row output signals having the same phase (delay time td2) and ultrasound vibrators corresponding to β2' row output signals in which the phase is inverted 180 degrees (delay time td2+T) relative to the signals output by the ultrasound vibrators corresponding to β1 row and β3 row (the relationship between signals from the ultrasound vibrators corresponding to γ1 row and γ3 row (delay time td3) and signals from ultrasound vibrators corresponding to γ2' row (delay time td3+T) is also similar).

In the case in which the operating mode is the first mode (for example, the SCW mode), the switch control part 1001 according to the Modified Example 2 first determines the type of the phase of signals that are output from each ultrasound vibrator based on reception delay time within received probe control data, and determines preamplifiers of the preamplifier group 103 which invert the phase 180 degrees based on the number of ultrasound vibrators corresponding to each phase and the number of adders 1042.

For example, in the case of the sub-arrays 102a1 to 102a3 included in the subgroup 102a as shown in FIG. 7, the number of the adders is three relative to six types of phases, and the number of types of phases exceeds the number of the adders. At this time, the body control circuit 21 controls each preamplifier of the preamplifier group 103 so as to invert the phase of signals from each ultrasound vibrator corresponding to α2' row, β2' row, and γ2' row of the sub-array 102a2, switches the bypass switch 1043 provided on the output side of the relevant preamplifier to the third contact point, and switches the other bypass switches 1043 to the second contact point.

Moreover, the switch control part 1001 receives the abovementioned control related to the inversion of the phase, and controls the matrix switch 1044 such that the signals having the predetermined same phase are input to the predetermined adder including the signals whose phase has been inverted.

FIG. 7 is described in detail as an example. For example, in FIG. 7, signals from the ultrasound vibrators corresponding to α1 row of the sub-array 102a1 and α3 row of the sub-array 102a3 and signals from the ultrasound vibrators corresponding to α2' row of the sub-array 102a2, whose phase has been inverted have the same phase (delay time td1), and they are input to the adder 1042a1 related to the relevant phase. Similarly, signals from the ultrasound vibrators corresponding to β1 row and β3 row and signals from the ultrasound vibrators corresponding to β2' row, whose phase has been inverted (delay time td2) are input to the adder 1042a2, and signals from the ultrasound vibrators corresponding to γ1 row and γ3 row and signals from the ultrasound vibrators corresponding to γ2' row, whose phase has been inverted (delay time td3) are input to the adder 1042a3.

Furthermore, the control of the preamplifier group 103 related to phase inversion and the control related to switching of the bypass switch 1043 to the third contact point or the second contact point may take a configuration in which the body control circuit 21 controls. In this case, the body control circuit 21 includes control signals regarding switching of the bypass switch 1043 in matrix switch control signals, and sends to the ultrasound probe 1. Moreover, similarly to the Modified Example 1, relating between subgroups and adders may be performed by the body control circuit 21.

Based on the above, according to the ultrasound probe according to the Modified Example 2, it becomes possible to add signals having 180 degree different phases by the same adder as the same signals by inverting the phase of signals from some of ultrasound vibrators. As shown in FIG. 7, with this, a phase can be set to each ultrasound vibrator more finely and flexibly than the ultrasound probe according to the first embodiment or the Modified Example 1. Moreover, in the first embodiment and the Modified Example 1, delay calculations (delay td and delay td+T) are performed separately with the body reception delay adding circuit 241; however, it becomes possible to process with the same delay calculation (delay td) in the Modified Example 2.

Furthermore, as the first operating mode, the SCW mode has been described as an example in the above; however, it is not limited to the SCW mode. It is possible to similarly apply to a mode in which the ultrasound vibrator group 102 is divided into operational regions with different purposes to use them.

Moreover, in this description, the example has been described in which as the configuration of the channel control circuits 104a to 104c, the sub-array reception beamformer group 1041, the bypass switch 1043, and the matrix switch 1044 are provided on the output side of the preamplifier group 103 in this order; however, it is not limited to this configuration.

Figure 8A:
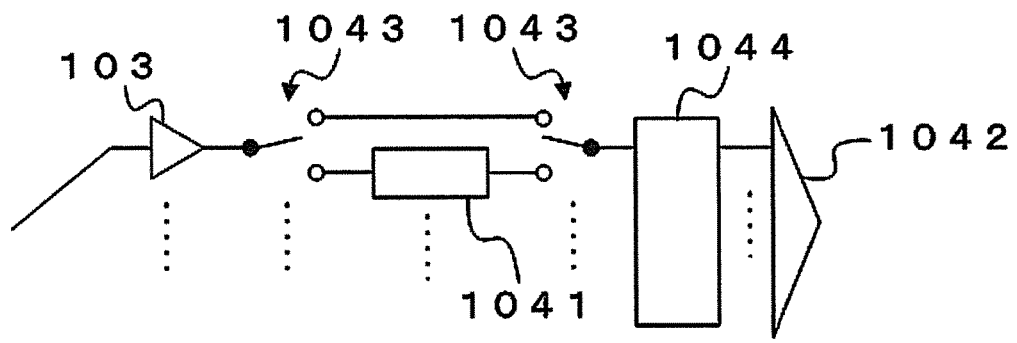
FIG. 8A shows an example of a circuit configuration of a channel control circuit according to an embodiment.
Figure 8B:
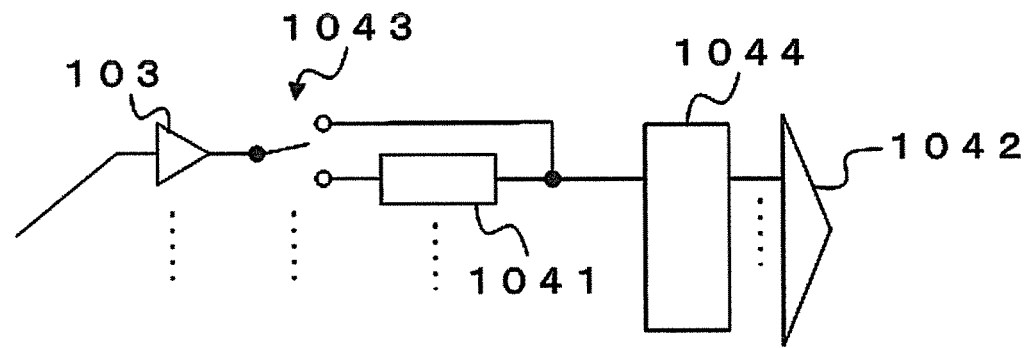
FIG. 8B shows an example of a circuit configuration of a channel control circuit according to an embodiment.
Figure 8C:
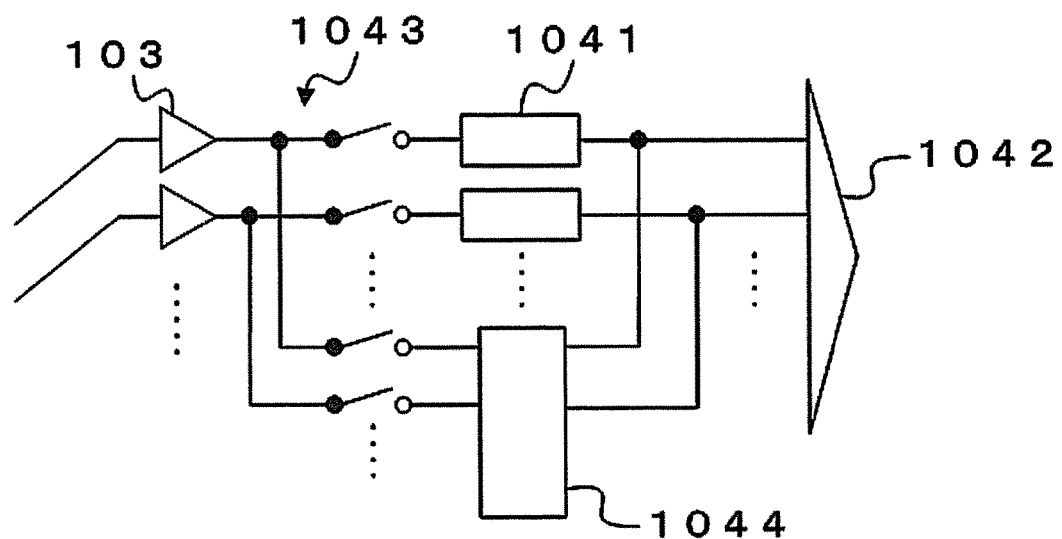
FIG. 8C shows an example of a circuit configuration of a channel control circuit according to an embodiment.
Figure 8D:
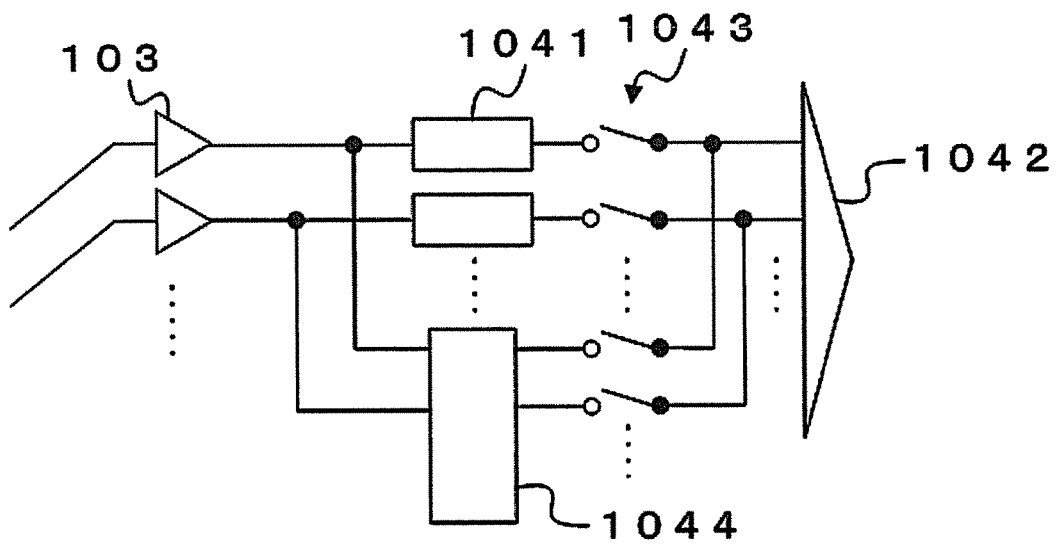
FIG. 8D shows an example of a circuit configuration of a channel control circuit according to an embodiment.

FIG. 8A to FIG. 8D are examples of the circuit configuration of the channel control circuit according to the present invention. For example, as shown in FIG. 8A, the bypass switch 1043 may be provided on both the input side and the output side of the sub-array reception beamformer group 1041, or may be provided on the input side of the sub-array reception beamformer group 1041 as shown in FIG. 8B and FIG. 8C. Moreover, as shown in FIG. 8C and FIG. 8D, the sub-array reception beamformer group 1041 and the matrix switch 1044 may be provided in parallel. As described above, as long as signals from each ultrasound vibrator can be input to the predetermined adder 1042 according to the operating mode, the circuit configuration of the channel control circuits 104a to 104c is not limited.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An ultrasound probe, comprising an ultrasound vibrator group, configured to a plurality of ultrasound vibrators that are aligned two-dimensionally, that send ultrasound and receive ultrasound echo signals reflected within a subject, a preamplifier that amplifies the received ultrasound echo signals for each of said ultrasound vibrators, and a beamformer group that performs delay processing on the ultrasound echo signals amplified by said preamplifier and that rectifies phases of said ultrasound echo signals output from a plurality of said ultrasound vibrators included in said ultrasound vibrator group, a bypass signal line that is brought out from an input side of said beamformer group and that bypasses said beamformer group, the ultrasound probe that outputs said ultrasound echo signals that have been received to an ultrasound diagnostic apparatus, further comprising:

a bypass switch connected to said preamplifier for connecting said bypass line in operating in a first mode to divide said plurality of ultrasound vibrators into a first set of ultrasound vibrators that send ultrasound and a second set of ultrasound vibrators that receive ultrasound in order to send and receive ultrasound and wherein said bypass switch is connected to said preamplifier for connecting said beamformer in operating in a second mode to send and receive ultrasound with said plurality ultrasound vibrators, an adder circuit that collects signals output from a plurality of said bypass switch into groups with the same phases to add and output them, and a matrix switch connects said bypass switch and said adder circuit, and that performs control such that the output from said bypass switch is input to said adder circuit, which is different for each of the phases, operating in said first mode.

2. The ultrasound probe according to claim 1, wherein the plurality of ultrasound vibrators that receive said ultrasound is divided into more than two subgroups including one or more of said ultrasound vibrators, and a combination of said beamformer group, said bypass switch, said matrix switch, and said adder circuit is placed for each of said subgroups, and wherein said matrix switch performs control such that output from said bypass switch included in said subgroups is input to said adder circuit, which is different for each of the phases, operating in said first mode.

3. The ultrasound probe according to claim 1, wherein some of said preamplifiers further invert the phases of ultrasound echo signals output from said ultrasound vibrators and output them, and wherein said bypass switch outputs either signals that have bypassed said beamformer or signals in which said preamplifiers have inverted the phases of said ultrasound echo signals, operating in said first mode, and said matrix switch controls such that an output that has bypassed said beamformer and an output in which said preamplifiers have inverted the phases of said ultrasound echo signals from said bypass switch are input to said adder circuit, which is different for each of the phases, operating in said first mode.

4. The ultrasound probe according to claim 1, 2 or 3 wherein said ultrasound probe has a first ultrasound vibrator group and a second ultrasound vibrator group, said plurality of ultrasound vibrators being any ultrasound vibrators that configure said first ultrasound vibrator group and said second ultrasound vibrator group.

5. An ultrasound diagnostic apparatus, comprising: an ultrasound probe comprising an ultrasound vibrator group, configured to a plurality of ultrasound vibrators that are aligned two-dimensionally, that send ultrasound and receive ultrasound echo signals reflected within a subject, a preamplifier that amplifies the received ultrasound echo signals for each of said ultrasound vibrators, and a beamformer group that performs delay processing on the ultrasound echo signals amplified by said preamplifier and that rectifies phases of said ultrasound echo signals output from a plurality of said ultrasound vibrators included in said ultrasound vibrator group, a bypass signal line that is brought out from an input side of said beamformer group and that bypasses said beamformer group, the ultrasound probe outputting said ultrasound echo signals, and an ultrasound diagnostic apparatus body receiving said ultrasound echo signals output from said ultrasound probe, the apparatus body performing phasing and adding processing on the ultrasound echo signals, the apparatus body generating an ultrasound image, wherein said ultrasound probe further comprises:

a bypass switch connected to said preamplifier for connecting said bypass line in operating in a first mode to divide said plurality of ultrasound vibrators into a first set of ultrasound vibrators that send ultrasound and a second set of ultrasound vibrators that receive ultrasound in order to send and receive ultrasound and wherein said bypass switch is connected to said preamplifier for connecting said beamformer in operating in a second mode to send and receive ultrasound with said plurality ultrasound vibrators, an adder circuit that collects signals output from a plurality of said bypass switch into groups with the same phases to add and output them, and a matrix switch connects said bypass switch and said adder circuit, and that performs control such that the output from said bypass switch is input to said adder circuit, which is different for each of the phases, operating in said first mode.

* * * * *